US00PP15335P2

(12) United States Plant Patent
Zary

(10) Patent No.: US PP15,335 P2
(45) Date of Patent: Nov. 16, 2004

(54) FLORIBUNDA ROSE PLANT NAMED 'JACTWIST'

(50) Latin Name: *Rosa hybrida*
Varietal Denomination: JACtwist

(75) Inventor: Keith W. Zary, Thousand Oaks, CA (US)

(73) Assignee: Jackson and Perkins Wholesale, Inc., Medford, OR (US)

( * ) Notice: Subject to any disclaimer, the term of this patent is extended or adjusted under 35 U.S.C. 154(b) by 22 days.

(21) Appl. No.: 10/300,568

(22) Filed: Nov. 19, 2002

(51) Int. Cl.[7] ..... A01H 5/00
(52) U.S. Cl. ..... Plt./145

(58) Field of Search ..... Plt./130, 134, 140, Plt./145, 143

(56) References Cited

U.S. PATENT DOCUMENTS

PP5,001 P * 3/1983 Warriner ..... Plt./145
PP5,248 P * 6/1984 Vargas ..... Plt./109

* cited by examiner

*Primary Examiner*—Howard J. Locker
(74) *Attorney, Agent, or Firm*—Klarquist Sparkman LLP

(57) ABSTRACT

Floribunda rose plant having upright, vigorous, branching growth; blooms in clusters of up to 3 to 7 flowers; light yellow flower color; dark green, healthy foliage; and sweet hyacinth like scent.

1 Drawing Sheet

Genus and species: *Rosa hybrida.*
Variety denomination: 'JACtwist'.

SUMMARY OF THE INVENTION

The present invention relates to a new and distinct variety of Floribunda rose plant named 'JACtwist' which was originated by me by crossing the variety 'JACjem', U.S. Plant Pat. No. 5,001, with the variety 'JACraw' (unpatented).

BACKGROUND OF THE INVENTION

The primary objective of this breeding was to produce a new rose variety having the healthy foliage, large clusters and yellow color of the female parent along with the vigor and fragrance of the unpatented male parent.

BRIEF SUMMARY OF THE INVENTION

The objective was substantially achieved, along with the other desirable improvements, as evidenced by the following unique combination of characteristics that are outstanding in the new variety and that distinguish it from its parents, as well as from all other varieties of which I am aware:

1. Upright, vigorous branching growth;
2. Blooms in clusters of 3 to 7 flowers;
3. Light yellow flower color;
4. Dark green, healthy foliage; and
5. Sweet hyacinth scent.

Asexual reproduction of this new variety by budding, as performed at Wasco, Calif., shows that the foregoing and all other characteristics and distinctions come true to form and are established and transmitted through succeeding propagations.

Comparison with Parents

The subject variety differs from the female parent in flower color, height and fragrance and differs from the red and white flower of the male parent.

Comparison with Similar Variety

The subject variety differs from other yellow floribundas in its light pale yellow color, its pink blush on aging and its very sweet, hyacinth fragrance.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (2001), except where ordinary dictionary significance of color is indicated.

Parentage:
*Seed parent.*—'JACjem' (U.S. Plant Pat. No. 5,001.
*Pollen parent.*—'JACraw' (unpatented).

Flower

Observations made from plants commencing at 2 years of age grown in a garden environment at Somis, Calif.

Blooming habit: Continuous.
Bud:
*Size:*—About 26 mm long and 22 mm in diameter when the petals start to unfurl.

*Form.*—The bud form is pointed ovoid.

*Color.*—When sepals first divide, bud color is Yellow Group 8C with prominent variegations of Greyed-Purple Group 185B on guard petals. When half blown, the upper sides of the petals are Yellow Group 10D becoming increasingly Yellow Group 9C toward base; and the lower sides of the petals are Yellow Group 10D with a larger portion of Yellow Group 9C.

*Sepals.*—Color: Upper surface: Green Group 143D. Lower surface: Green Group 143C with prominent portions Greyed-Purple Group 183B. Length: 28–34 mm. Width: 8–10 mm. Shape: Subulate. Surface texture: Upper surface: Hoary. Lower surface: Glandular. There are three lightly appendaged sepals. There are two unappendaged sepals with ciliate edges.

*Receptacle.*—Color: Yellow-Green Group 144A. Shape: Funnel. Size: Small, about 6 mm long×8 mm wide. Surface: Smooth.

*Peduncle.*—Length: Medium, averaging about 6 cm. Surface: Glandular. Color: Yellow-Green Group 144B with overlay of Greyed-Purple Group 183B. Strength: Stiff and erect.

Bloom:

*Size.*—Medium. Average open diameter is about 8–10 cm.

*Borne.*—In flat clusters of 3–7 blooms,

*Stems.*—Strength: Normal. Average length is about 25–35 cm with a diameter of 5–8 mm.

*Form.*—When first open: High centered. Permanence: Flattens.

*Petalage.*—Number of petals under normal conditions: 35–40.

*Color.*—The upper sides of the petals are Yellow Group 11D. The reverse sides of the petals are Yellow Group 10D. The base of each petal has Yellow Group 7C spot. The major color on the upper side is Yellow Group 11D.

*Discoloration.*—The general tonality at the end of the first day: Yellow Group 11D. At the end of the third day: Yellow Group 11D with variegations of Red Group 50D. As petal ages, variegations tend increasingly toward Red Group 49A.

*Fragrance.*—Moderate, sweet and buttery (hyacinth like).

Petals:

*Texture.*—Thin.

*Shape.*—Between obovate and obdeltoid.

*Surface.*—Smooth.

*Margin.*—Entire. Apex Shape: Obtuse. Base Shape: Cuneate.

*Form.*—Flat.

*Arrangement.*—Imbricated.

*Petaloids.*—Number: 3 to 5. Color: Tips Red Group 49C, mid portion Yellow Group 11D and base Yellow Group 9B.

*Persistence.*—Petals drop off cleanly before drying.

*Lastingness.*—On the plant: Fair (about 5–6 days). As a cut flower: Fair (about 6–7 days).

Reproductive parts:

*Stamens.*—Number: 80–100. Length: 10–12 mm. Arrangement: Regular around styles. Anthers: Length: 2 mm. Color: Yellow-Orange Group 21C. Filaments: Color: Yellow-Orange Group 14C. Length: 8–10 mm. Pollen: Color: Greyed-Orange Group 164B.

*Pistils.*—Number: 60–80. Length; 6–7 mm. Styles: Color: Green-Yellow Group 1D. Length: 5–6 mm. Stigmas: Color: Greyed-Orange Group 163C. Length: 1 mm.

*Hips.*—None present.

PLANT

*Form.*—Bush.

*Growth.*—Vigorous, upright, branching.

*Mature plant.*—Height: 120 cm at two years of age. Width: 80 cm.

*Rootstock.*—Dr. Huey.

Foliage: Number of leaflets on normal mid-stem leaves; 5 or 7.

*Size.*—Medium (12 cm long×9 cm wide).

*Quantity.*—Abundant.

*Color.*—New foliage: Upper side: Greyed-Purple Group 183A. Lower side: Greyed-Purple Group 183A. Old foliage: Upper side: Green Group 139A. Lower side: Yellow-Green Group 147B.

Leaflets:

*Size.*—About 40 mm long×35 mm wide.

*Shape.*—Orbicular.

*Base shape.*—Rounded.

*Apex Shape.*—Cupsidate.

*Texture.*—Leathery, glossy.

*Edge.*—Serrated.

*Serrations.*—Single, small.

*Petiole.*—Color: Yellow-Green Group 146C.

*Petiole rachis.*—Color: Yellow-Green Group 146B. Underside: Smooth with occassional prickles.

*Auricle shape.*—None present.

*Stipules.*—Length: 16–18 mm, smooth but with many glands along the edge.

*Disease resistance.*—Resistant to mildew and rust and susceptible to blackspot under normal growing conditions.

*Pest persistence.*—Not tested.

*Vein color.*—Yellow-Green Group 147B.

*Venation pattern.*—Reticulate.

Wood:

*New wood.*—Color: Greyed-Red Group 178A. Bark: Smooth.

*Old wood.*—Color: Green Group 139B. Bark: Smooth.

Prickles:

*Quantity.*—On main canes from base: Ordinary (20–25 every 15 cm). On laterals from main canes: Ordinary (7–8 every 15 cm).

*Form.*—Hooked downward.

*Length.*—7–10 mm.

*Color when young.*—Greyed-Purple Group 183A.

*Color when mature.*—Greyed-Orange Group 164A.

Small prickles:

*Quantity.*—On main stalks: None. On laterals: None.

Winter hardiness: Hardy to Zone 5.

I claim:

1. A new and distinct variety of rose plant of the floribunda class, substantially as herein shown and described, characterized particularly by upright, vigorous, branching growth; blooms in clusters of up to 3 to 7 flowers; light yellow flower color; dark green, healthy foliage; and sweet hyacinth like scent.

* * * * *

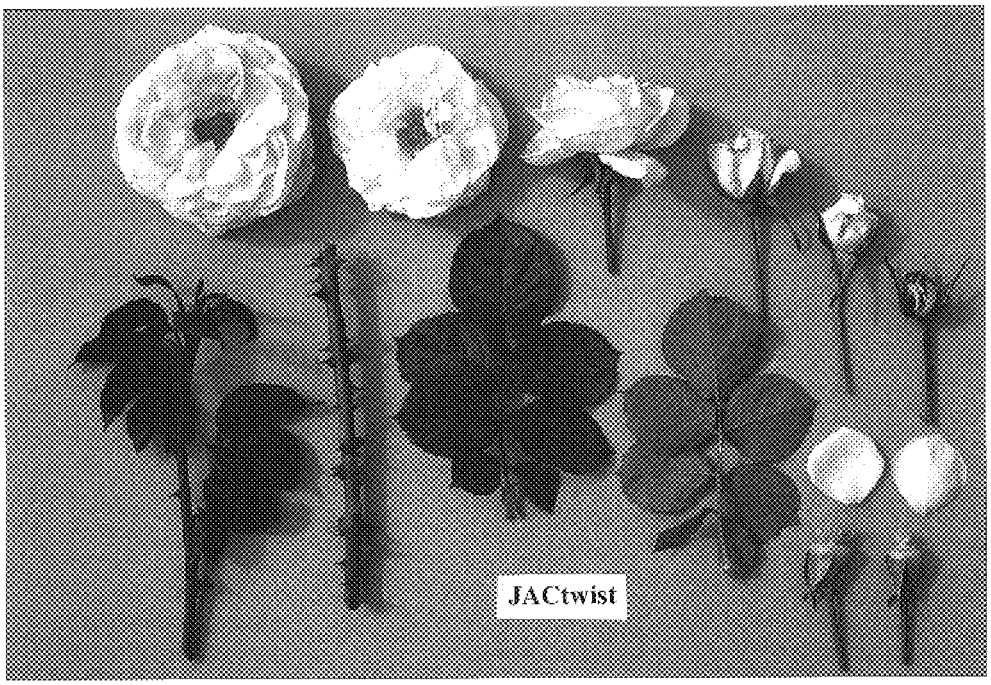
JACtwist